United States Patent
Wang et al.

(10) Patent No.: US 9,047,318 B2
(45) Date of Patent: Jun. 2, 2015

(54) REAL-TIME CLOUD IMAGE SYSTEM AND MANAGING METHOD THEREOF

(71) Applicant: NATIONAL TAIWAN UNIVERSITY OF SCIENCE AND TECHNOLOGY, Taipei (TW)

(72) Inventors: Ching-Wei Wang, Taipei (TW); Chu-Mei Hung, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 156 days.

(21) Appl. No.: 13/890,477

(22) Filed: May 9, 2013

(65) Prior Publication Data

US 2014/0126841 A1    May 8, 2014

(30) Foreign Application Priority Data

Nov. 8, 2012    (TW) .............................. 101141605 A (51) Int. Cl.
  *G06K 9/60*    (2006.01)
  *G06F 17/30*    (2006.01)
  *G06F 19/00*    (2011.01)

(52) U.S. Cl.
  CPC .... *G06F 17/30247* (2013.01); *G06F 17/30265* (2013.01); *G06F 19/321* (2013.01)

(58) Field of Classification Search
  CPC .................. G06F 17/30247; G06F 17/30265; G06F 19/321; G06T 7/00
  USPC .................. 382/232, 276, 305; 358/403, 404; 707/821, 825, 827, 829, 831
  See application file for complete search history.

(56) References Cited

U.S. PATENT DOCUMENTS

| | | | |
|---|---|---|---|
| 8,010,555 B2 | 8/2011 | Eichhorn | |
| 2005/0091672 A1 | 4/2005 | Debique et al. | |
| 2007/0036462 A1 | 2/2007 | Crandall et al. | |
| 2007/0217699 A1 * | 9/2007 | Mahiar et al. | 382/232 |
| 2008/0232658 A1 | 9/2008 | Sugaya et al. | |
| 2009/0299771 A1 | 12/2009 | Hsieh et al. | |
| 2010/0045698 A1 * | 2/2010 | Shields et al. | 345/629 |
| 2010/0077358 A1 * | 3/2010 | Sugaya et al. | 715/838 |
| 2011/0130642 A1 | 6/2011 | Jaeb et al. | |
| 2013/0077892 A1 * | 3/2013 | Ikeno et al. | 382/286 |

FOREIGN PATENT DOCUMENTS

| | | |
|---|---|---|
| CN | 101217643 A | 7/2008 |
| CN | 102368779 A | 3/2012 |
| TW | I343798 B | 6/2011 |
| TW | I351647 B | 11/2011 |
| TW | I358652 B | 2/2012 |

* cited by examiner

*Primary Examiner* — Ali Bayat (74) *Attorney, Agent, or Firm* — Birch, Stewart, Kolasch & Birch, LLP (57) ABSTRACT

A real-time cloud imaging system includes at least a frontend device and a backend system. The frontend device generates an instruction message and a ROI (Region of Interest) message, and the backend system is coupled to the frontend device. The backend system has at least a raw image, wherein the raw image has a plurality of images of different resolutions. Each of the images and the raw image are composed of a plurality of tiles. The ROI message corresponds to a region of interest respectively within each of the images and the raw image. The backend system, according to the instruction message and the ROI message, selectively provides a grouping of the tiles within the region of interest of the raw image or one of the images to the frontend device.

13 Claims, 11 Drawing Sheets

| Level | Dimension | Capacity | Image Resolution | Ratio of Total Capacity |
|---|---|---|---|---|
| 0 | 120000 by 80000 | 29GB | 1:1 | |
| 1 | 30000 by 20000 | 1.8GB | 4:1 | 6% |
| 2 | 7500 by 5000 | 112MB | 16:1 | 0.4% |
| 3 | 1875 by 1250 | 7MB | 64:1 | 0.024% |
| Lowest Resolution | 1024 by 680 | 2MB | 117:1 | 0.00725% |

REAL-TIME CLOUD IMAGE SYSTEM AND MANAGING METHOD THEREOF

BACKGROUND OF THE INVENTION

1. Field of the Invention

The present invention generally relates to a real-time cloud image system and managing method thereof; particularly, the present invention relates to a real-time cloud imaging system and managing method thereof that can display, process, and analyze ultra-high resolution images.

2. Description of the Related Art

For many years, medical pathology departments have been slow in updating their equipments, resulting in the continued use of conventional pathology optical microscopes. This not only results in more human errors in judgments and ineffective data management to occur, data storage is also of concern. Along with the increased popularity of digital pathology images in recent years, fast and objective analysis of digital pathology images may be conducted. As well, the physical storage space once required to store physical pathology images can be significantly decreased. In recent years, digitalization of pathology slide images has become an area of great activity. However, in terms of sharing high resolution pathology images on the cloud, problems of slowness or delays from use of the system often occurs due to a bottleneck in the technology. In addition, the conventional cloud system lacks smart recognition and comparison technologies to help medical experts with clinical diagnostics or research analysis.

SUMMARY OF THE INVENTION

It is an object of the present invention to provide a real-time cloud image system and managing method thereof that can increase data transfer speed and decrease wait times of data transfers by decreasing the image sizes that are transferred.

It is another object of the present invention to provide a real-time cloud image system and managing method thereof that can decrease the amount of data transfer and image analysis/processing needed while also enable parallel processing of the data such that the speed at which images are displayed, analyzed, and processed can be increased.

The real-time cloud image system includes at least a frontend device and a backend system. The frontend device generates an instruction message and a ROI (Region of Interest) message, and the backend system is coupled to the frontend device. The backend system has at least a raw image, wherein the raw image has a plurality of images of different resolutions. Each of the images and the raw image are composed of a plurality of tiles. The ROI message corresponds to a region of interest respectively within each of the images and the raw image. The backend system, according to the instruction message and the ROI message, selectively provides a grouping of the tiles within the region of interest of the raw image or one of the images to the frontend device.

The managing method of the real-time cloud image system includes: (A) receiving in the backend system a ROI (Region of Interest) message from the frontend device; (B) selecting one of the image levels of the pyramid structure as a designated image level according to the ROI message in the backend system, and then determining a position of a region of interest in the designated image level; and (C) receiving an instruction message in the backend system from the frontend device, and selectively transmitting a grouping of the tiles within the region of interest of the designated image level to the frontend device.

DETAILED DESCRIPTION OF THE PREFERRED EMBODIMENT

The present invention provides a real-time cloud image system and managing method thereof for the displaying, sharing, processing, and analyzing of high volumes of high or low resolution images on a cloud network (including private networks, local networks, and public networks). The real-time cloud imaging system includes at least a frontend device and a backend system. The frontend device generates an instruction message and a ROI (Region of Interest) message, and the backend system is coupled to the frontend device. The backend system has a backend database storing a plurality of object data (such as medical records data) and their respective large volume high or low resolution image data, such as large volume high resolution pathology images. Each image has a plurality of images of different resolutions. Each of the images and the raw image are composed of a plurality of tiles. The backend system can in real-time provide medical data and their high resolution pathology images to the frontend device so that the frontend device may display the medical data and the pathology images. The frontend device may instruct the backend system to provide in real-time the plurality of tiles of the high resolution pathology images such that portions of the image may be quickly retrieved, without wasting too much memory, through high speed parallel processing. The ROI message corresponds to a region of interest respectively within each of the images and the raw image. The backend system, according to the instruction message and the ROI message, selectively provides a grouping of the tiles within the region of interest of the raw image or one of the images to the frontend device. Alternatively, the backend system may instead process and/or analyze the grouping of the tiles within the region of interest of the raw image or one of the images. During the high speed parallel processing, the data of the tiles may be individually retrieved and processed, wherein it is transmitted to an individual processing core and undergoes parallel high speed multi-core processing.

Figure 1:
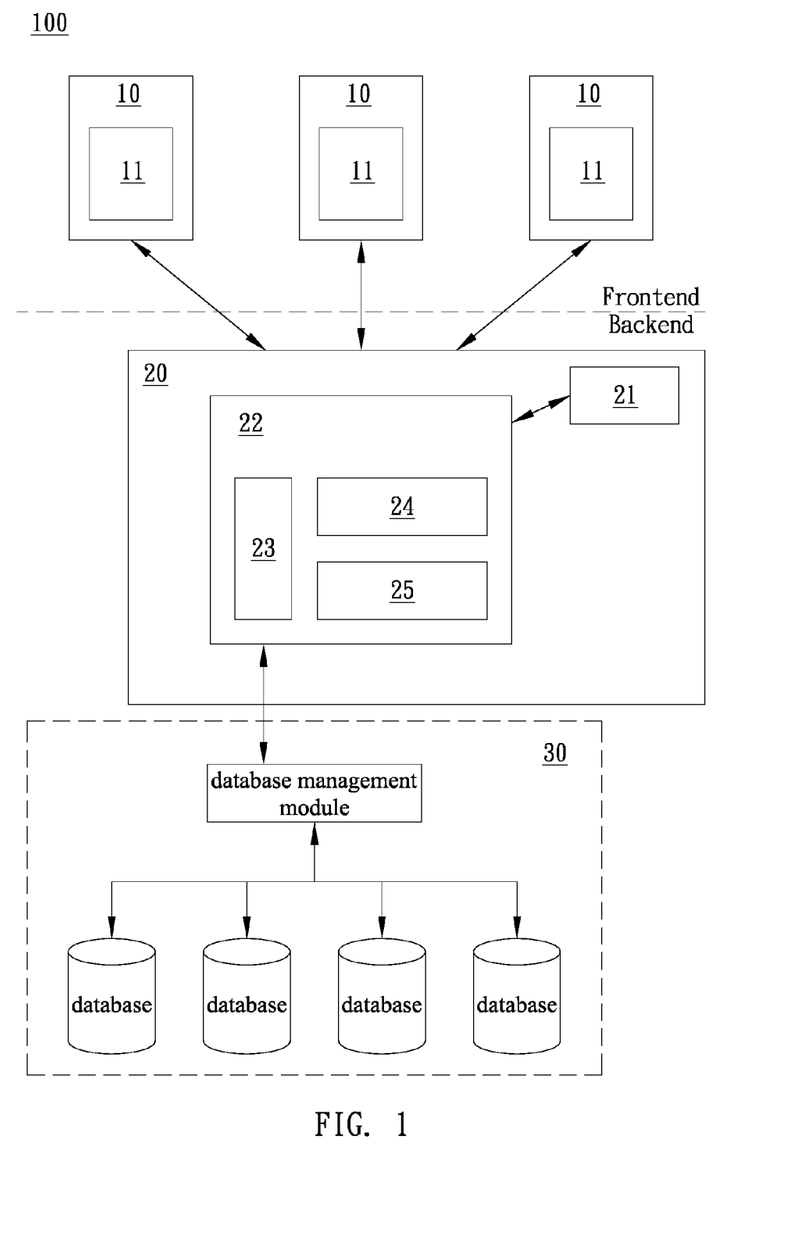
FIG. 1 is an embodiment of a physical structure of the real-time cloud imaging system.

FIG.1 illustrates an embodiment of the real-time cloud imaging system 100 of the present invention. As shown in FIG.1, the real-time cloud imaging system 100 includes at least a frontend device 10, a backend system 20, and at least a backend database 30. In the present embodiment, each frontend device 10 and backend database 30 is coupled to the backend system 20. In a preferred embodiment, the frontend device 10 may include desktop computers, laptop computers, smart phones, and tablet computers. The frontend device 10 has a user interface 11 for inputting commands or instructions from users, as well as for displaying data. The frontend device 10 is preferably coupled to the backend system 20 through a network, such as the Internet. However, in other different embodiments, the frontend device 10 may also be coupled to the backend system 20 through wireless or non-wireless local area networks. In a preferred embodiment, the real-time cloud imaging system 100 of the present invention is used for displaying, sharing, analyzing, and processing medical images. Through the real-time cloud imaging system 100, users may quickly and conveniently diagnose, analyze, or process medical data such as pathology images (ex. medical slide images) after being authenticated (through accounts and password protections). The real-time cloud imaging system can decrease the time required for the display, analyze, or processing of images.

As shown in FIG. 1, the backend system 20 includes at least a processor 21 and at least a main memory 22, wherein the main memory 22 stores at least an operating system 23, at least an application program 24, and at least a database management system 25. In a preferred embodiment, the backend system 20 is a type of server system, including one or a plurality of servers. In the present embodiment, the backend system 20 may be a Apache HTTP server, although it is not restricted to this. The operating system 23 executes the Apache operating system to provide the frontend device 10 different types of web services. The application program 24 can include application programs providing services for PHP, JavaScript, and FLASH web pages. However, in other different embodiments, the backend system 20 may be other types of servers, such as a ASP (Active Server Page) web service server of Microsoft.

As shown in FIG. 1, in the present embodiment, the database management system 25 is another type of application program acting as an interface for the application program 24 to use the backend database 30. The backend database 30 may include one or many physical storage devices. In the present embodiment, no matter how many physical storage devices there are in the backend database 30, in terms of software, the backend database 30 is realized through SQL(Structured Query Language) or MySQL. However, the backend database 30 is not limited to these forms. In the present example, the MySQL database of the backend database 30 may be used with the Apache web server, PHP, JavaScript, and Flash such that the backend system 20 can provide the frontend device 10 web services as well as data stored on the backend database 30. However, in other different embodiments, if the backend system 20 does not use Apache, the backend database 30 may also be in other forms, such as Microsoft's Access databases, SQL databases, or Oracle databases.

Figure 2:
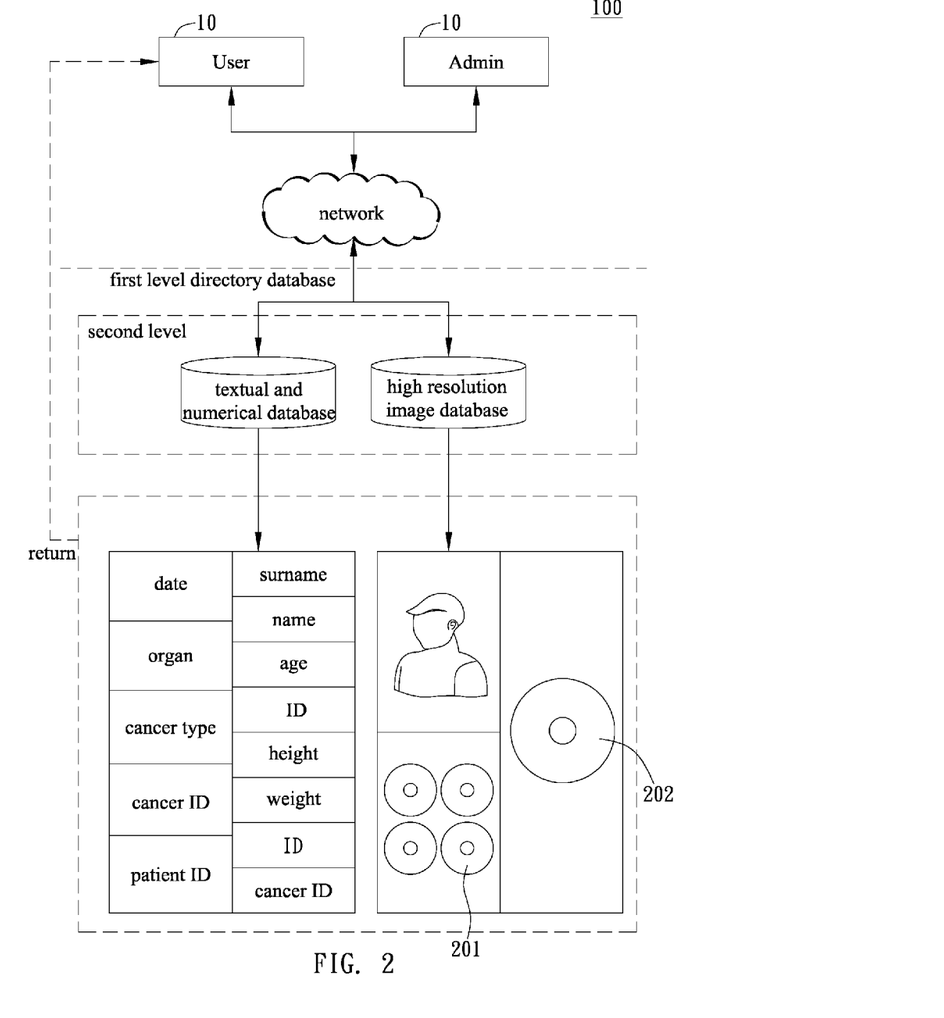
FIG. 2 is another embodiment of the real-time cloud imaging system.

FIG. 2 is an illustration introducing the functions of the real-time cloud high resolution imaging system 100. As shown in FIG. 2, when the frontend device 10 is connected to the backend system 20 through a network, the frontend device 10 can log into the backend system 20 through a user account or administrator account. After the frontend device 10 has logged into the backend system 20, the user of the frontend device 10 can operate the frontend device 10 through its interface, such as requesting data stored in the backend database 30 from the backend system 20. As shown in FIGS. 1 and 2, when the frontend device 10 is logged into the backend system 20, the user of the frontend device 10 will enter a Layer 1 of the backend system 20. According to the User Id, passport, and/or any other related login information, the real-time cloud imaging system 100 can selectively allow the user to pass Layer 1 and connect to a Layer 2. In the present embodiment, the second layer includes a word or number database (ex. electronic diagnostic medical records database) and a high resolution database (ex. high resolution pathology image database. The high resolution image database can be a database for high resolution multimedia images. In other words, layer 1 and layer 2 form the backend database 30 of FIG. 1, wherein layer 1 is a directory of the integrated database. As shown in FIG. 2, Layer 2 stores data of the backend database 30. For instance, as shown in FIG. 2, texts or numerical databases such as electronic medical records may include different information, such as name, age, medical record number, height, weight, cancer identification number, diagnostic data, caregiver's name, cancer type, diagnostic result (good or bad), and other information related to the patient. For example, the high resolution (medical) image database stores high resolution (pathology) images of the patients.

In another embodiment, the frontend device 10 can only request medical history data and pathology image data that the account and password used to log into the backend system 20 has privilege for. However, when the frontend device 10 is logged into the backend system 20 with the administrator account, the backend system 20 will allow the frontend device 10 privileges of uploading, deleting, and downloading of data. In the present embodiment, the administrator account privileges can allow the frontend device 10 to update or amend any data on the backend database 30.

Figure 3:
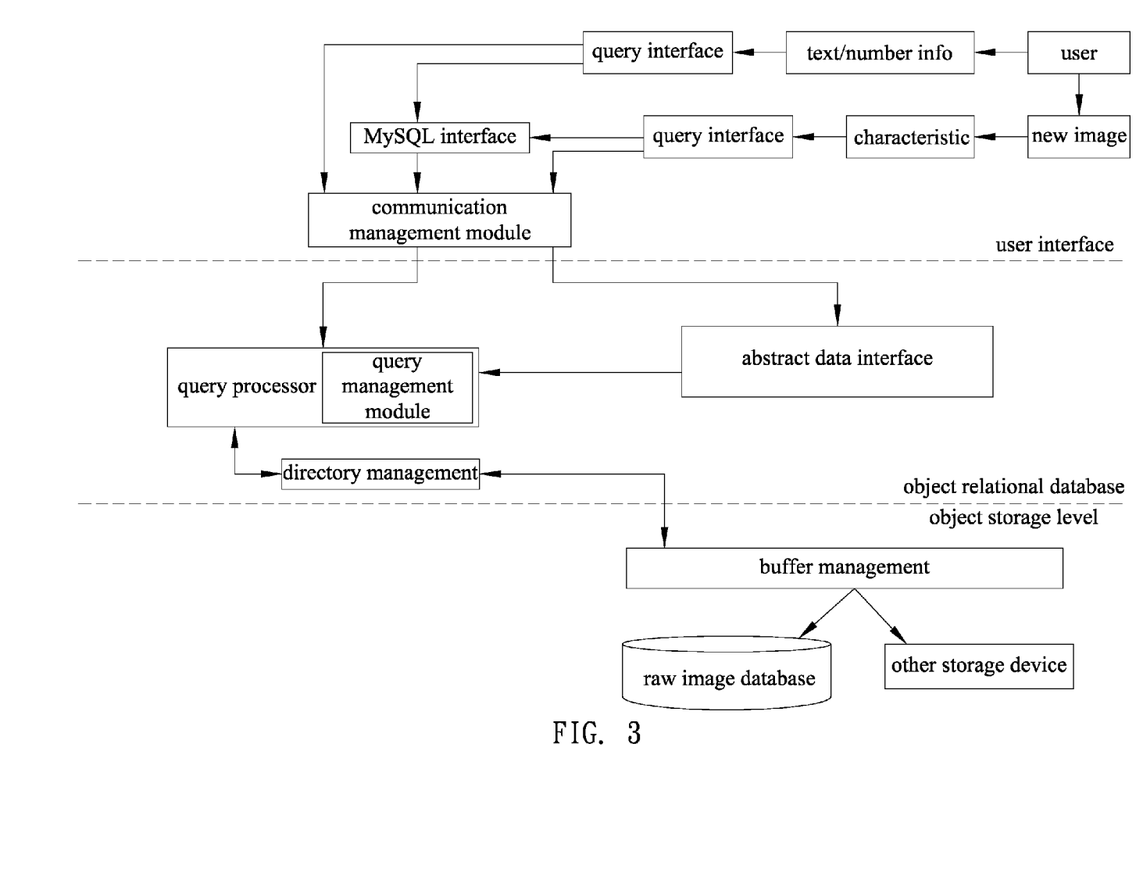
FIG. 3 is another embodiment of the real-time cloud imaging system.

FIG. 3 is another illustration of FIGS. 1 and 2. As shown in FIG. 3, a user interface level is shown in the frontend device 10. In the user interface level, users may use a query interface to communicate with the backend system 20. In more definite terms, as shown in FIG. 3, since the frontend device 10 is preferably connected to the backend system 20 through a network, users may connect to the communication management module of the backend system 20 through the communication management module of the frontend device 10 through the communication coordination between the query interface and the frontend device 10. In the present embodiment, the communication management module is preferably a network interface card that uses HTTP (hypertext transfer protocol) network communication protocols. In the present embodiment, the frontend device 10 uses a browser to communicably connect with the backend system 20 through the network communication protocol. The browser of the frontend device 10 may include Opera, Google Chrome, Microsoft Explorer, Apple corporation's Safari, or any other related browsers. However, in other different embodiments, the frontend device 10 may install an application programming interface (API) corresponding to the backend system 20. In this circumstance, there may be a MySQL database interface between the query interface and the communication management module in order to provide the frontend device 10 a direct way to convert and send the data query instructions of the user into MySQL format to the backend system 20 for further processing. The advantage of this is that the burden on the backend system 20 can be decreased, resulting in quicker responses by the backend system 20 to the frontend device 10. For instance, if the user logs into the backend system 20 through the frontend device 10 under the administrator account, when the user wants to upload new images or data to the backend system 20, the frontend device 10 can directly command the backend database 30 through the MySQL interface to store the data at a specific place.

As shown in FIG. 3, the Object storage layer represents the physical storage device of the backend database 30. In the present embodiment, the backend database 30 includes a buffer management module for buffering and managing the storage and transmitting of data of the database. As shown in FIG. 3, the buffer management module is connected to at least a raw image database and another storage device. The raw image database can include a plurality of storage servers and is used for storing raw files of pathology image data. The other storage device may include serial hard drive storage devices or any other storage devices.

As shown in FIG. 3 of the textual and numerical query, the image database has search capabilities. The search capabilities may be defined respectively as a normal search and an advanced search. In a normal search of the electronic medical records database, a single patient data (such as surname or age) may be selected to undergo searching. The advanced search, on the other hand, may allow multiple criteria of the patient data (such as surname and age) to be entered for the search. A single criterion (such as organ or cancer) may be selected to execute normal search of the patient pathology (slide) data. Multiple criteria (such as organ and cancer) may be selected to execute advanced search. As shown in FIG. 3 of the image search, the user inputs an image and then a new image characteristic is automatically detected. A characteristic is inputted into the query interface, whereby any image data matching the characteristic inputted is found and shown.

Figure 4:
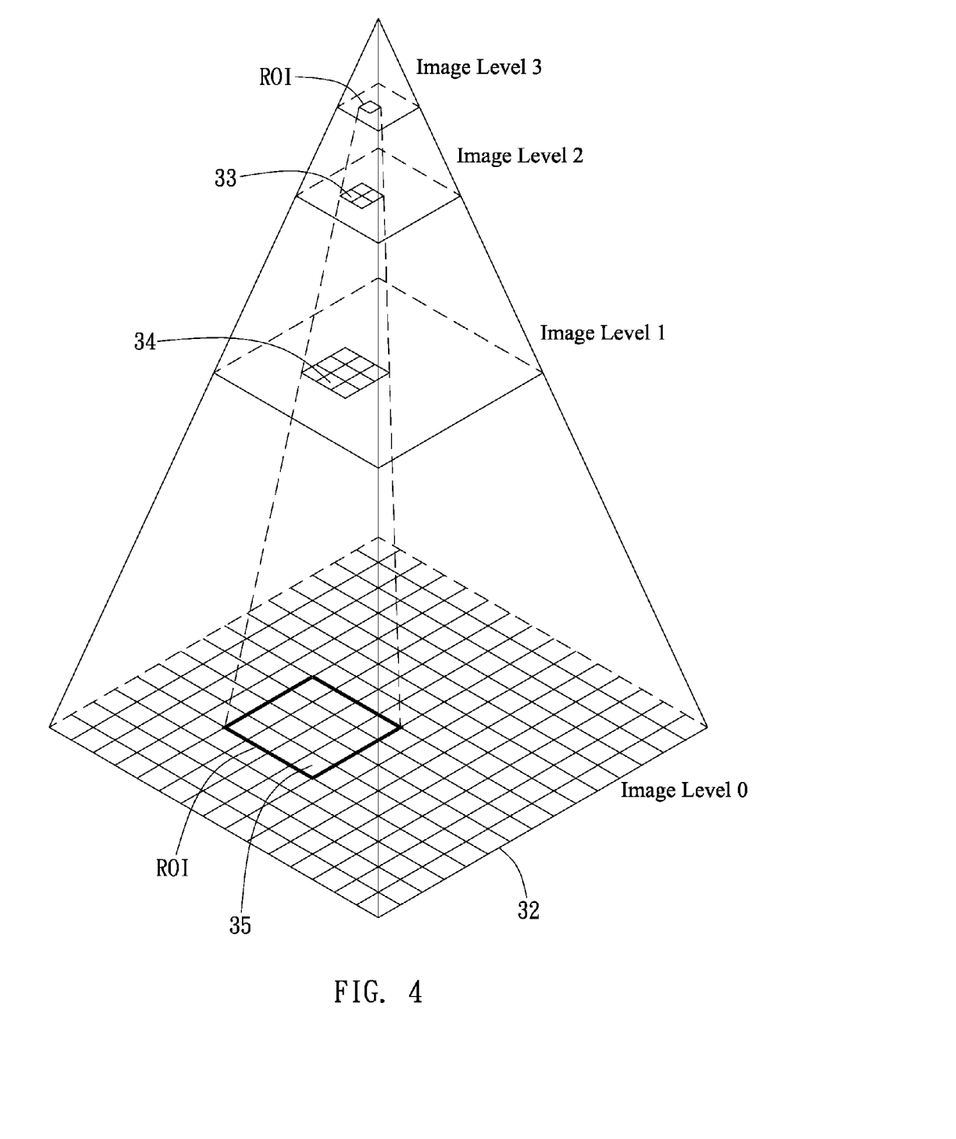
FIGS. 4 is an embodiment of the hierarchical multi-resolution (pathology) image pyramid for individual high resolution image data.

FIG. 4 illustrates an embodiment of a file structure having different resolutions of a single high resolution pathology image file provided by the real-time cloud (high resolution) imaging system 100. As shown in FIG. 4, image level 0 (bottom level) of the pyramid structure is the highest resolution of the raw pathology image 32 stored in the backend database 30. In the present embodiment, the raw pathology image 32 has the highest resolution, wherein the raw pathology image 32 is composed of a plurality of tiles 35. In a preferred embodiment, the resolution of the image will decrease moving up through the levels in the pyramid structure (ie. the dimension of the image will shrink). In the present embodiment, when the user logs into the backend system 20 through the frontend device 10 and requests the pathology data, the backend system 20 will by default transmit the highest image level tile data of the raw pathology image to the frontend device 10 so that the frontend device 10 can quickly display the image without delay. More concretely in terms of FIG. 4 as an example, the third image level in the present embodiment is the highest image level of the pyramid structure. When the frontend device 10 logs into the backend system 20 for the first time and requests for the pathology data, the backend system 20 will transmit the entire image level of the third image level to the frontend device 10. The frontend device 10 will then receive and display the image of the entire image level on the user interface (ex. display monitor) of the frontend device 10. In this manner, the real-time cloud imaging system 100 can decrease the amount of data transferred since the backend system 20 does not transmit the highest resolution of the raw pathology image of the first image level to the frontend device 10. In addition, the real-time cloud imaging system 100 can at the same time also save on the amount of time for the frontend device 10 to download and process the image. In other words, the burden on the frontend device 10 and the backend system 20 can be decreased. In the present embodiment, the default highest image level is the third image level. However, it should be noted that although FIG. 4 only illustrates 4 levels (image levels 0-3), in other different embodiments, the image resolution pyramid structure of the real-time cloud imaging system 100 can include more or less image levels. In other words, there may be many image levels of different resolutions between the highest image level and the lowest image level (image level 0). It should be noted that within the same pathology image pyramid, the image content of each image level are similar to each other except that they all have different image resolutions.

When the frontend device 10 quickly retrieves and displays the image of the default highest image level (lowest resolution pathology image of the image level 0), users may select a ROI (Region of Interest) on the displayed image of the highest image level by touching the spot on the user interface of the frontend device 10. In the present embodiment, the area and size thereof included by the ROI may be defined by the user. For instance, users may draw a square shaped area of ROI on the image of the high image level on the user interface. This area represents the section that the user wishes to view. The frontend device 10 will generate an image position instruction according to the position of the ROI designated by the user. The image position instruction is used for notifying the backend system 20 information related to the selected ROI area, such as the size, range, the relative position of the ROI within the image level, the shape of the outlined area, and any other related information.

After selecting or drawing out the ROI and generating the image position instruction, users may instruct the frontend device 10 to display the other higher resolution images corresponding to the indicated ROI. In more definite terms, the frontend device 10 will generate an instruction message to the backend system 20 according to the designated ROI and the pathology image level currently being displayed on the frontend device 10. In the present embodiment, users may select different levels of resolutions, such as the resolutions of image level 0, 1, or 2. Accordingly to the selection, the backend system 20 will compute, according to the image level indicated by the instruction message and the ROI, the position on the image level corresponding to the ROI as well as the tiles on the image level to which it overlaps with. The backend system 20 will then accordingly retrieve from the backend database 30 the group of tiles of higher resolution in the indicated image level associated with the ROI and then transmit them to the frontend device 10. For instance, if the frontend device 10 currently displays the default lowest resolution of the pathology image (image level 3 of FIG. 4), when the frontend device 10 transmits the image position instruction to the backend system 20 and the user has selected an image level of higher resolution (a lower image level in the pyramid structure), the backend system 20 will transmit the group of tiles of the selected image level of higher resolution (such as image level 2) that correspond with the ROI to the frontend device 10. In other words, as shown in FIG. 4, when the frontend device 10 is at an image level of higher resolution (such as image level 3), users can indicate the range of the ROI and select a lower image level of higher resolution (image level 2, 1, or 0) so that the backend system 20 will transmit the corresponding group of tiles (35, 34, or 33) on the indicated image level that is associated with the ROI to the frontend device 10. For instance, users may select image level 1 such that the backend system 20 will correspondingly transmit the tile 34 associated with the ROI from the backend database 30 to the frontend device 10.

In another embodiment, the frontend device 10 can allow users to selectively activate an image analysis processing mode so that the frontend device 10 will generate and transmit an instruction message including an image analysis processing instruction to the backend system 20. When the backend system 20 receives from the frontend device 10 the ROI, the image level selection made by the user, and the image analysis processing instruction, the backend system 20 will according to the selected ROI schedule priority to processing the image content of the group of tiles of the designated image level adjacent to the ROI and the group of tiles within the ROI of the image levels above and below the designated image level in the pyramid structure, such that the processed image content may be used as pre-fetch data for the frontend device 10. In this manner, the real-time image display, processing, and analysis may be achieved by the real-time cloud imaging system 100. In addition, when the individual tiles are being processed by the backend, parallel processing may be employed. For instance, if the image displayed by the frontend device 10 is the group of tiles 34 corresponding to the ROI in image level 1 of FIG. 4 and the image analysis processing mode is activated, the backend system 20 will accord priority to processing the group of tiles 34 adjacent to the ROI as well as the group of tiles 33 and 35 corresponding to the ROI in the image level 2 and 0. In this manner, under the pretense that the frontend device 10 is displaying the image of the tile 34 corresponding to the ROI, users may execute a drag instruction on the display of the frontend device 10 to instruct the frontend device 10 to display tiles 34 that are adjacent and outside of the ROI range in the direction of the dragging movement. Since the backend system 20 has already pre-processed those adjacent tiles 34 as pre-fetch data and sent them to the frontend device 10, the frontend device 10 is able to immediately display the data that the user wants when the user initiates the dragging motion. In the present embodiment, dragging motion or dragging movement refers to conventional techniques of sliding a finger in a direction on the screen of the frontend device 10. However, in other different embodiments, users may utilize other different methods of input to the drag motion, such as scroll keys or buttons. In the above example, if the user instead selects a resolution of the upper or lower image level, the frontend device 10 will display the pre-fetch data of the tiles 33 and 35 that were pre-processed by the backend system 20. In this manner, the wait time or lag experienced by the frontend device 10 in the real-time cloud imaging system 100 may be decreased. Under parallel processing, the tile data can be independently retrieved and process, and can be individually transmitted to a single processor core to undergo high speed multi-core parallel processing.

Figure 5A:
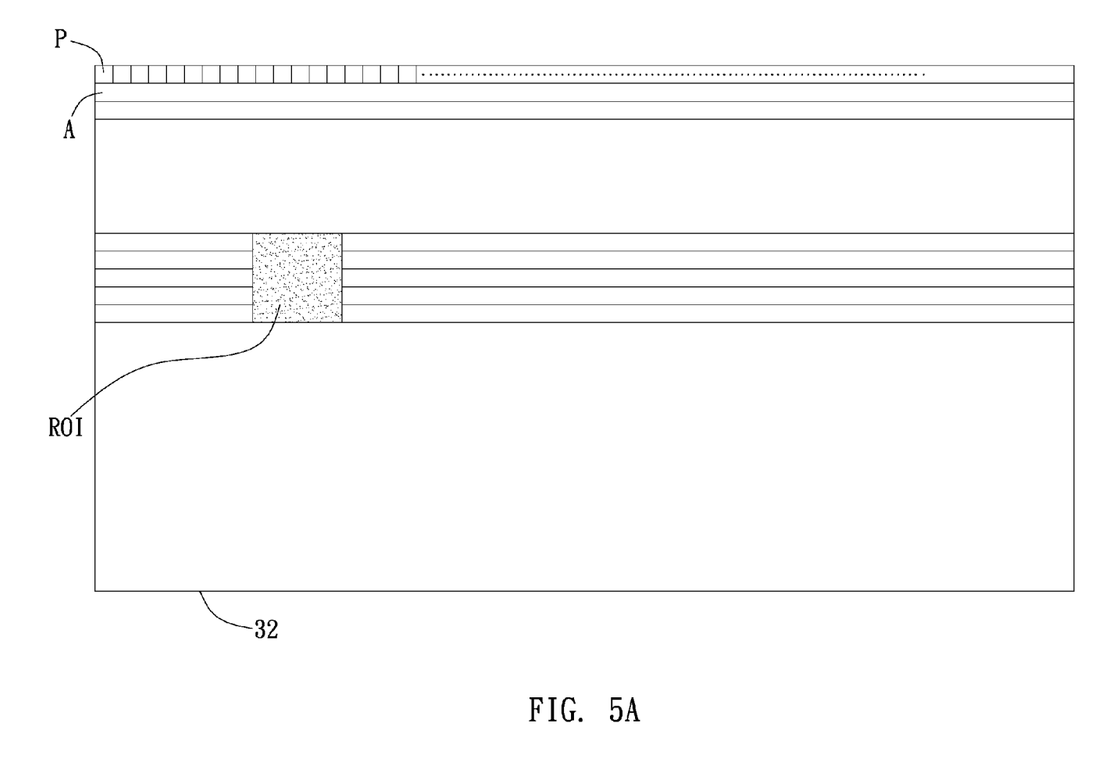
FIG. 5A is an embodiment of the conventional stripped organization for pixel storage that requires to load a large amount of the image data with a number of rows in order to access the ROI region.
Figure 5B:
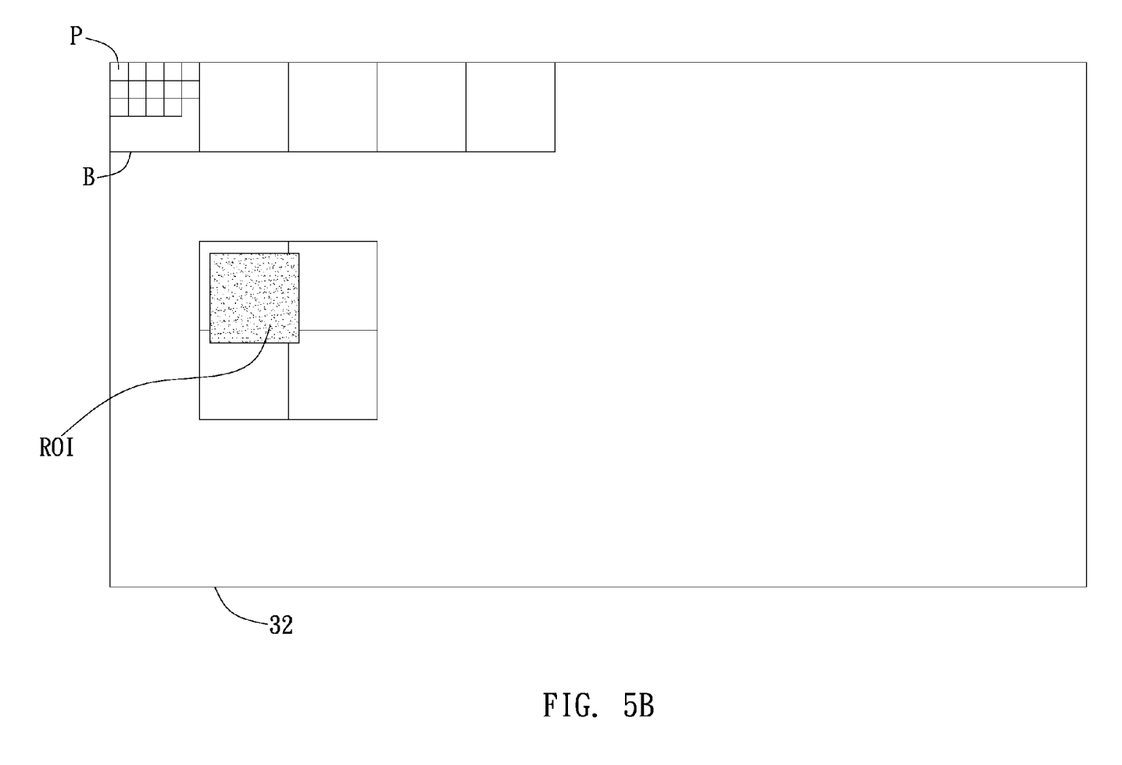
FIG. 5B is an embodiment of the tiled organization for pixel storage that requires a small amount of the image data in order to access the ROI region.

FIG. 5A illustrates the relationship between the pixels P of the raw high resolution pathology image 32 and the ROI. If plurality of pixels P are grouped or assembled as a plurality of rows A (as shown in FIG. 5A, each pixel P is assigned a row A), the ROI indicated by the user will cover or overlap a plurality of rows A. When transmitting the image data to the frontend device 10, the backend system 20 must transmit in entirety of all rows A that the ROI fully or partially covers. This method wastes time and resources since the backend system 20 also transmits pixels P that aren't covered by the ROI (but are still in the same rows A as the pixels P that are covered by the ROI). Therefore, as shown in FIG. 5B, each image level of the high resolution image is assembled from tiles such that each tile B includes N×M amounts of pixels P, wherein N and M are positive integers. For example, as shown in FIG. 5B, each tile B can include an assembly of 256×256 ($2^8 \times 2^8$) pixels P. And as shown in FIG. 5B, when the area covered by the ROI overlaps with a plurality of tiles B (as shown in FIG. 5B of the four tiles B), the backend system 20 can image process, analysis, or share the four tiles B to the frontend device 10. In a preferred embodiment, each high resolution image file has a plurality of image levels of different resolutions, wherein the shapes of the tiles of the pathology image of each image level of image resolution is a quadrilateral shape, such as a square or rectangular shape. However, in other different embodiments, the dimension and shape to assemble or group the pixels P may be varied. In addition, the shape of the tiles of each image level may also change according to design requirements.

Figure 5C:
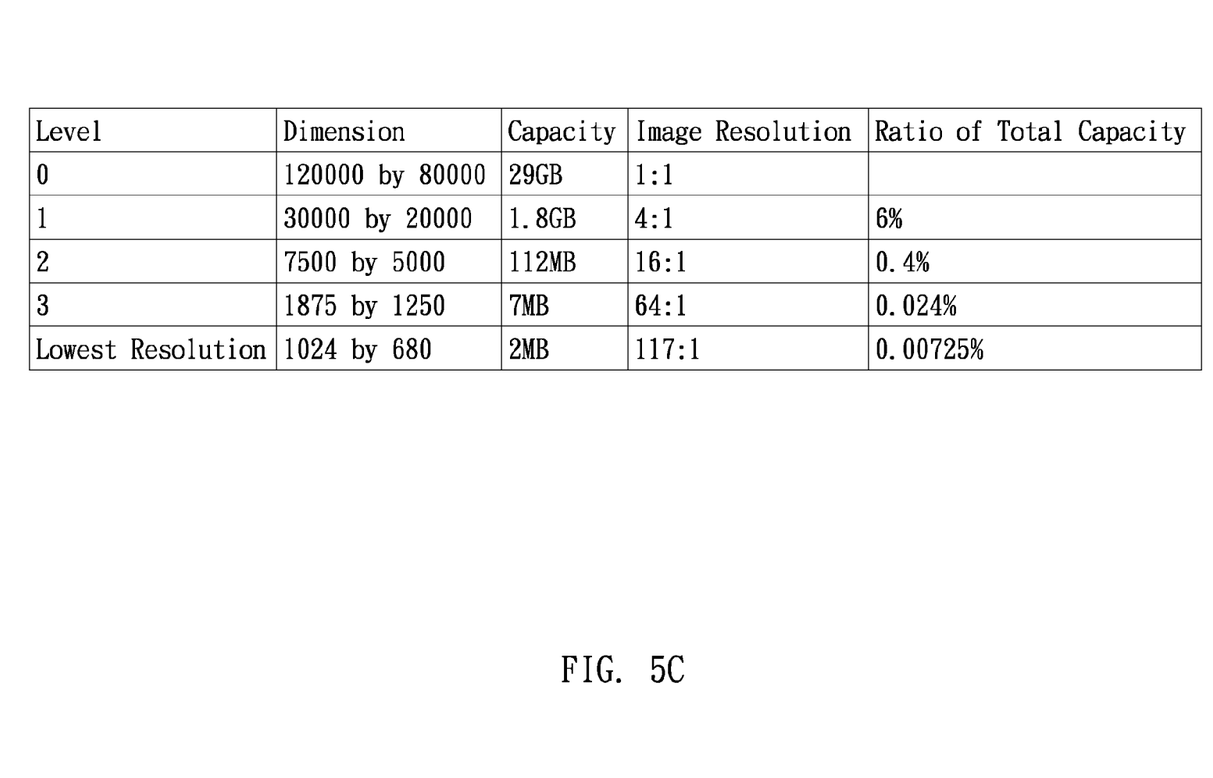
FIG. 5C is an embodiment of the relationship between the raw (pathology) image, different resolutions of the image, and the image size.

FIG. 5C illustrates an example of the relationship between each level of image resolution of the pathology images and the increase in the amount of data. As shown in FIG. 5C, suppose the dimension of the highest resolution image 32 (image level 0) is 1,200,000×80,000 pixels and the data of the image amounts to 29 GB. If the dimension of image level 1 is 30,000×2,000 pixels, then the amount of data would be 1.8 GB. This can then be extrapolated to the other image levels. In terms of the present embodiment, by decreasing the data amount to only 6.5%, the system can be quicker in the retrieving, transmitting, displaying, analyzing, and processing of the image data (the related plurality of tile data) associated with the ROI of the indicated resolution (specific image level). This can significantly decrease the amount of image data as well as the time that the frontend device 10 wastes on downloading of the image data. In turn, the speed, the usability, and the convenience of the real-time cloud imaging system 100 may be increased.

Figure 6:
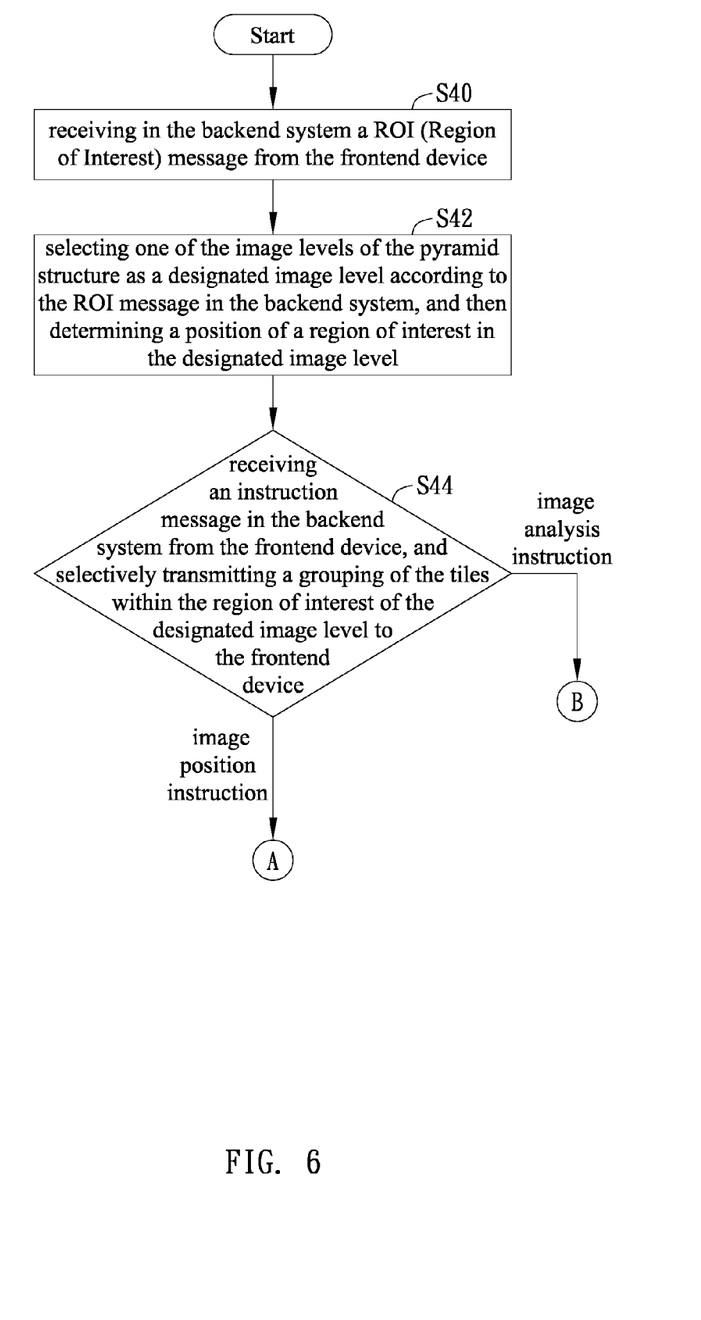
FIGS. 6-9 are flowchart diagrams embodiments of the managing method of the real-time cloud imaging system.

FIGS. 6 to 9 are flowchart diagrams for the managing method of the real-time cloud imaging system of the present invention. In the present embodiment, the managing method includes the following steps:

As shown in FIG. 6, step S40 includes receiving in the backend system 20 a ROI (Region of Interest) message from the frontend device 10. In the present embodiment, users may select or draw an area of interest (ie. ROI) through the user interface of the frontend device 10. The frontend device 10 will generate the ROI message according to the drawn or selected area of interest. In more concrete terms, in an embodiment, when the user queries for medical data and the raw pathology image thereof after logging into the backend system 20 through the frontend device 10, the backend system 20 will by default first transmit the highest image level (lowest resolution of the raw pathology image) of the pyramid structure corresponding to the raw pathology image to the frontend device 10. At this time, the user in front of the frontend device 10 may select, circle, or draw the ROI area through the use of the user interface of the frontend device 10 on the displayed lowest resolution pathology image. The frontend device 10 will then generate the ROI message according to the ROI drawn or selected by the user.

Step S42 includes selecting one of the image levels of the pyramid structure as a designated image level according to the ROI message in the backend system 20, and then determining a position of a region of interest in the designated image level. In more concrete terms, the frontend device 10 will notify the backend system 20 of the image level that the user is currently viewing. For instance, if the pathology image currently being viewed on the frontend device 10 corresponds to a middle image level in the pyramid structure (medium resolution of the pathology image), the ROI message will include this information such that the backend system 20 may set that image level as the designated image level. After selecting the designated image level, the backend system 20 will determine on the designated image level the position corresponding to the ROI. As shown in FIG. 4, if the designated image level is image level 1, the backend system 20 will according to the ROI defined by the user on the highest image level (lowest resolution of the pathology image of FIG. 3) determine the associated position on the designated image level of image level 1.

Step 44 includes receiving an instruction message in the backend system 20 from the frontend device 10, and selectively transmitting a grouping of the tiles within the region of interest of the designated image level to the frontend device 10. In terms of the above example, as shown in FIG. 4, after the backend system 20 has determined the ROI area in the designated image level, the backend system 20 will determine which grouping of tiles of the designated image level lie within the determined ROI area. The backend system 20 will then transmit the grouping to the frontend device 10. In this manner, the frontend device 10 may be able to display the grouping of image tiles on its screen and/or user interface.

Figure 7:
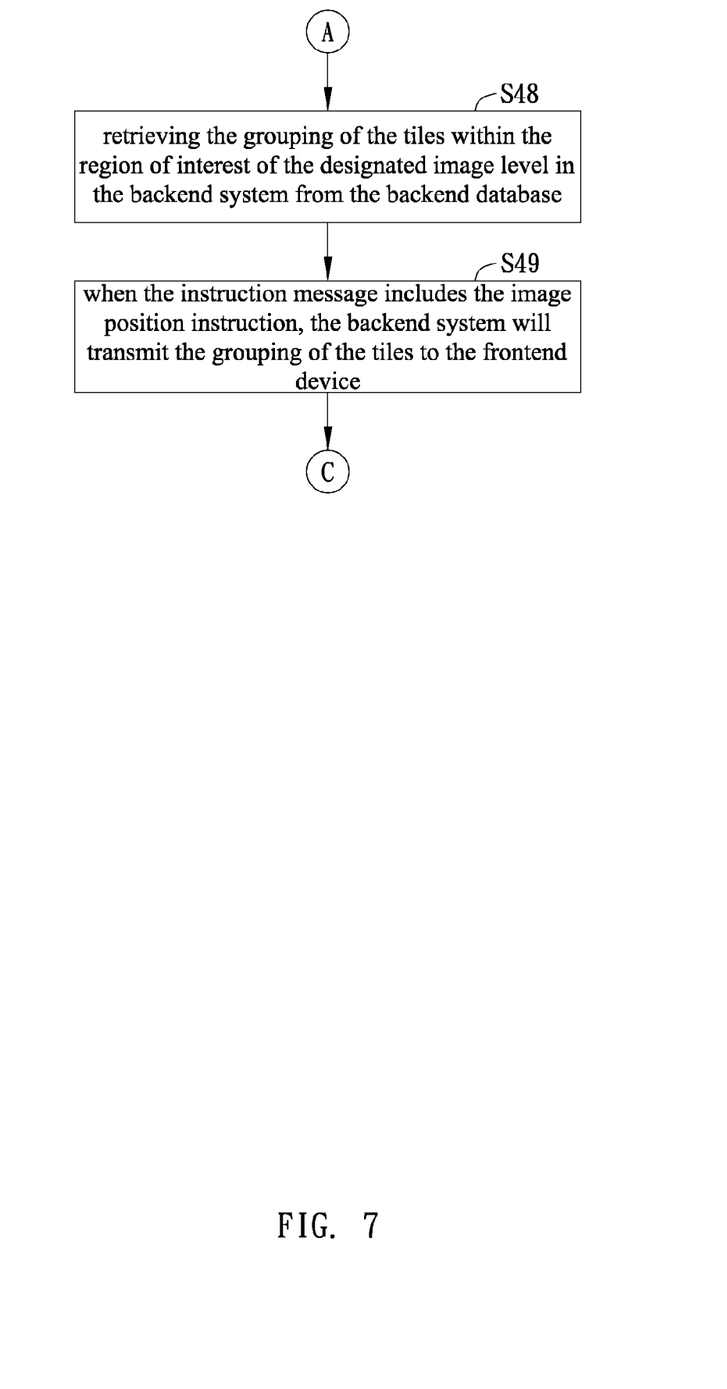

FIG. 7 is a flowchart diagram of step S44 of FIG. 6, wherein the instruction message includes image position instruction. As shown in FIG. 7, step S48 includes retrieving the grouping of the tiles within the region of interest of the designated image level in the backend system 20 from the backend database 30. In more definite terms, in Step S44, the backend system 20 will store the grouping of tiles in the backend database 30 after the backend system 20 has determined the group. Afterwards, the backend system 20 can freely at any time retrieve the grouping of data from the backend database 30. In step S49, when the instruction message includes the image position instruction, the backend system 20 will transmit the grouping of the tiles to the frontend device 10. For instance, in terms of FIG.4 as an example, if the designated level is image level 1, the backend system 20 will transmit the grouping of tiles 34 within the ROI of the image level 1 to the frontend device 10 after the backend system 20 has received the instruction message containing the image position instruction.

Figure 8:
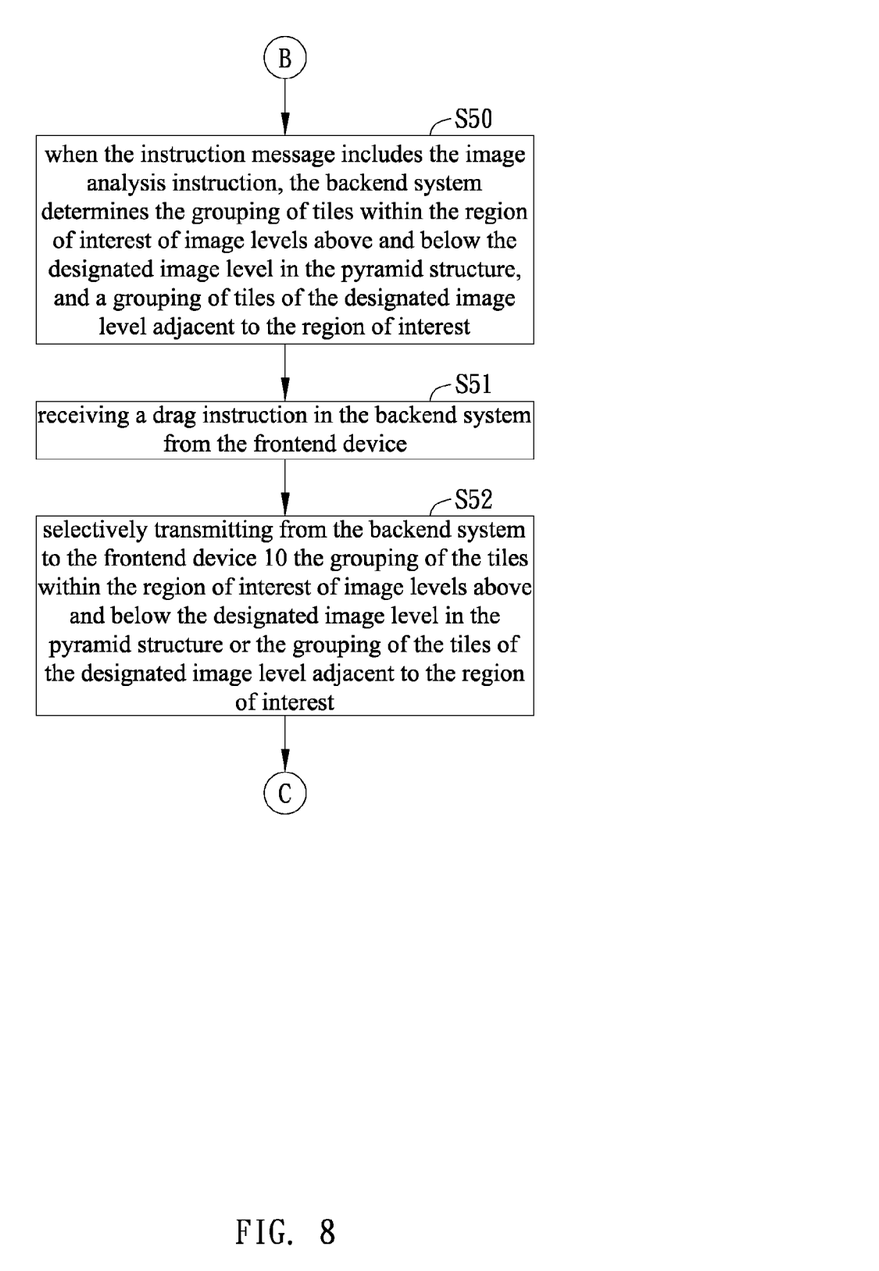

FIG. 8 is a flowchart diagram of step S44 of FIG. 6, wherein the instruction message includes an image analysis instruction. As shown in FIG. 8, in step S50, when the instruction message includes the image analysis instruction, the backend system 20 will determine the grouping of tiles within the region of interest of image levels above and below the designated image level in the pyramid structure, and a grouping of tiles of the designated image level adjacent to the region of interest. In more definite terms, using image level 1 of FIG. 4 as the designated image level as an example, when the backend system 20 receives from the frontend device 10 the instruction message having the image analysis instruction, the backend system 20 will first determine the corresponding region of interest (ROI) on the image levels directly above and below the designated image level. Then, the backend system 20 will store the grouping of tiles that lie within those regions of interests in the backend database 30. In other words, as shown in FIG. 4, the backend system 20 will store these grouping of tiles in the backend database 30 so that the frontend device 10 may retrieve and display them later on. Alternatively, the backend system 20 may also transmit the grouping of tiles to the frontend device 10. In this present embodiment, as shown in FIG. 4, the backend system 20 will transmit to the frontend device 10 the grouping of tiles 33 in the image level covered by the ROI in FIG. 2 and the grouping of tiles 35 that is completely or partially covered by the ROI in image level 0. In this manner, the grouping of tiles sent to the frontend device 10 acts as a form of pre-fetch data for the frontend device 10 to display. In addition, the backend system 20 can also determine and store the grouping of tiles 34 adjacent and outside of the ROI area on the designated image level 1 in the backend database 30. In this manner, the response time of sending results of image analysis to the frontend device 10 may be decreased.

Step S51 includes receiving a drag instruction in the backend system 20 from the frontend device 10. In the present embodiment, users may execute a drag instruction on the displayed pathology image on the frontend device 10, such as a drag motion or movement to the right hand direction of the frontend device 10 on the pathology image. The frontend device 10 will generate and transmit to the backend system 20 the drag instruction according to the drag motion or movement. In the present embodiment, users may change the position on the display image through the drag motions. However, in other different embodiments, users may use other different forms to instruct the frontend device 10 to change the resolution of displayed pathology image.

Step S52 includes selectively transmitting from the backend system 20 to the frontend device 10 the grouping of the tiles within the region of interest of image levels above and below the designated image level in the pyramid structure or the grouping of the tiles of the designated image level adjacent to the region of interest. In more definite terms, according to the determination in step S51 of the grouping of the tiles and the grouping of tiles adjacent to the ROI in the designated image level, these groupings of the tiles may be selectively transmitted to the frontend device 10 by the backend system 20 as pre-fetch data. For instance, if users do a drag motion on the displayed pathology image of the designated image level on the frontend device 10, the backend system 20 will transmit to the frontend device 10 the grouping of the tiles adjacent to the ROI on the designated image level that is in the direction of the drag motion. In other different embodiments, the backend system 20 can also transmit to the frontend device 10 all tiles adjacent outside of the ROI on the designated image level. In this circumstance, when the user does the drag motion, the frontend device 10 will immediately display the tiles that are adjacent and outside of the ROI in the direction of the drag motion since those tiles were already transmitted to the frontend device 10. In another embodiment, users may change the resolution of the display. In more definite terms, when the user selects the ROI and gives the instruction to increase or decrease the resolution of the pathology image, the backend system 20 can predetermine and process the groupings of tiles above and below the designated image level according to step S51 and then send them to the frontend device 10.

Figure 9:
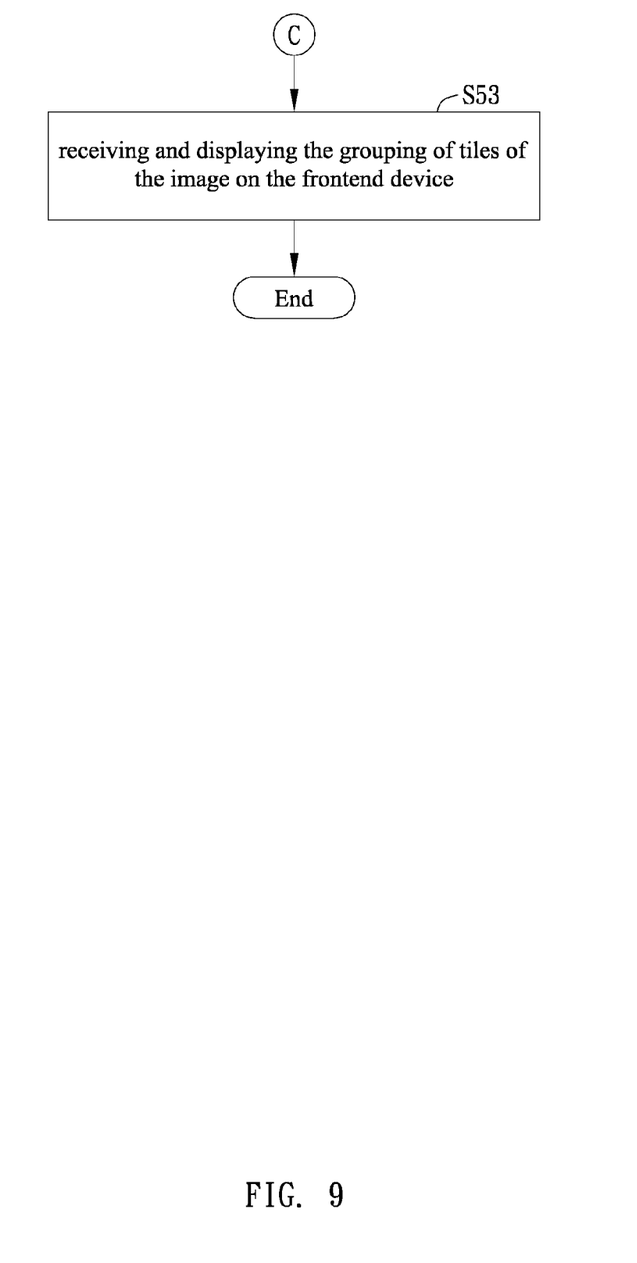

FIG. 9 is a flowchart diagram of the last step S53 of the managing method of the present invention. As shown in FIG. 9, step S53 includes receiving and displaying the grouping of tiles of the image on the frontend device 10. In more definite terms, the frontend device 10 will display on its user interface the grouping of the tiles received from the backend system 20. For instance, as shown in FIG. 4, if the grouping of tiles 35 within the ROI in the image level 0 is transmitted to the frontend device 10 by the backend system 20, the frontend device 10 will display the grouping on its user interface. In this manner, the backend system 20 can decrease the amount of data transfer as well as decrease the amount of image data displayed by the frontend device 10 such that the function of real-time displaying, processing, and analyzing of pathology images may be accomplished.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A real-time cloud image system, comprising:
   at least a frontend device generating an instruction message and a ROI (Region of Interest) message; and
   a backend system coupled to the frontend device, the backend system having at least a raw image, wherein the raw image has a plurality of images of different resolutions, each of the images and the raw image are composed of a plurality of tiles, and the tiles are quadrilateral shapes;

wherein the ROI message corresponds to a region of interest respectively within each of the images and the raw image, the backend system according to the instruction message and the ROI message selectively provides a grouping of the tiles formed from neighboring tiles in the region of interest of the raw image or one of the images to the frontend device.

2. The real-time cloud image system of claim 1, wherein the raw image and the images are sequentially arranged by resolution in a pyramid structure having a plurality of image levels, with the raw image having the highest resolution and acting as the lowest bottom image level of the pyramid structure.

3. The real-time cloud image system of claim 2, wherein the image levels include at least an image of medium or low resolution, the backend system determines a designated image level from the image levels according to the instruction message and the ROI message and selectively provides to the frontend device the tiles within the region of interest of the designated image level, a grouping of the tiles within the region of interest of image levels above and below the designated image level in the pyramid structure, or a grouping of the tiles of the designated image level adjacent to the region of interest.

4. The real-time cloud image system of claim 1, wherein the raw image and the plurality of images are pathology images.

5. The real-time cloud image system of claim 1, wherein the frontend device includes a desktop computer, a laptop computer, a smart phone, or a tablet computer.

6. The real-time cloud image system of claim 1, wherein the frontend device further includes a user interface for displaying one of the raw image, one image from the plurality of images, and a portion of the raw image or a portion of the images.

7. The real-time cloud image system of claim 1, wherein the frontend device is coupled to the backend system through an internet network.

8. The real-time cloud image system of claim 1, further comprising at least a backend database, wherein the backend database stores the raw image, the images, and a plurality of medical records.

9. A managing method of a real-time cloud image system, wherein the real-time cloud image system includes at least a frontend device and a backend device, the backend system has at least a raw image and a plurality of images having different resolutions and corresponding to the raw image, the raw image and the plurality of images are composed of a plurality of tiles, the images are arranged in sequence by resolution in a pyramid structure having a plurality of image levels with the raw image having the highest resolution and acting as the lowest bottom image level of the pyramid structure, the managing method comprising:

(A) receiving in the backend system a ROI (Region of Interest) message from the frontend device;

(B) selecting one of the image levels of the pyramid structure as a designated image level according to the ROI message in the backend system, and then determining a position of a region of interest in the designated image level; and (C) receiving an instruction message in the backend system from the frontend device, and selectively transmitting a grouping of the tiles within the region of interest of the designated image level to the frontend device when the instruction message includes an image position instruction.

10. The managing method of claim 9, wherein the backend system comprises a backend database that stores the raw image and the images; before transmitting the grouping of the tiles within the region of interest of the designated image level to the frontend device, the managing method further includes retrieving the grouping of the tiles within the region of interest of the designated image level in the backend system from the backend database.

11. The managing method of claim 9, further comprising receiving and displaying an image of the grouping of the tiles in the frontend device.

12. The managing method of claim 9, wherein the instruction message includes an image analysis instruction; in step (C), when the instruction message includes the image analysis instruction, the backend system determines a grouping of tiles within the region of interest of image levels above or below the designated image level in the pyramid structure and a grouping of tiles of the designated image level adjacent to the region of interest.

13. The managing method of method 12, further comprising:

receiving a drag instruction in the backend system from the frontend device; and selectively transmitting from the backend system to the frontend device the grouping of the tiles within the region of interest of image levels above and below the designated image level in the pyramid structure or the grouping of the tiles of the designated image level adjacent to the region of interest.

* * * * *